United States Patent
García-Delgado Banchs et al.

(10) Patent No.: US 12,129,229 B2
(45) Date of Patent: Oct. 29, 2024

(54) AMAROUCIAXANTHIN A ESTERS AND USES THEREOF

(71) Applicant: GAT THERAPEUTICS, S.L., Barcelona (ES)

(72) Inventors: Noemí García-Delgado Banchs, Barcelona (ES); Eugènia Ruiz Cánovas, Barcelona (ES); Jaume Mercadé Roca, Barcelona (ES)

(73) Assignee: GAT THERAPEUTICS, S.L., Barcelona (ES)

( * ) Notice: Subject to any disclaimer, the term of this patent is extended or adjusted under 35 U.S.C. 154(b) by 0 days.

(21) Appl. No.: 18/558,067

(22) PCT Filed: Jul. 18, 2022

(86) PCT No.: PCT/EP2022/070001
§ 371 (c)(1),
(2) Date: Oct. 30, 2023

(87) PCT Pub. No.: WO2023/285703
PCT Pub. Date: Jan. 19, 2023

(65) Prior Publication Data
US 2024/0239733 A1    Jul. 18, 2024

(30) Foreign Application Priority Data
Jul. 16, 2021   (EP) ..................... 21382644

(51) Int. Cl.
*C07C 49/242* (2006.01)
*A61K 31/122* (2006.01)

(52) U.S. Cl.
CPC .......... *C07C 49/242* (2013.01); *A61K 31/122* (2013.01); *C07B 2200/09* (2013.01)

(58) Field of Classification Search
CPC .. C07C 49/242; A61K 31/122; C07B 2200/09
See application file for complete search history.

(56) References Cited

FOREIGN PATENT DOCUMENTS

| CN | 112804996 A | 5/2021 |
|---|---|---|
| CN | 115715804 A | 2/2023 |
| EP | 3705109 A1 | 9/2020 |

OTHER PUBLICATIONS

Takao Matsuno, "Carotenoids of Tunicates7 111. The Structural Elucidation of Two New Marine Carotenoids, Amarouciaxanthin A and B," J Nat Prod, Jul. 1985, pp. 606-613, vol. 48, No. 4.

(Continued)

*Primary Examiner* — Deborah D Carr
(74) *Attorney, Agent, or Firm* — Piloff Passino & Cosenza LLP; Rachel K. Piloff; Sean A. Passino

(57) ABSTRACT

The present invention relates to compound of formula (I) or a stereoisomer thereof, in particular amarouciaxanthin A acetate. The invention also relates to the method of preparation of these compounds, to compositions comprising them as well as their medical and cosmetic uses.

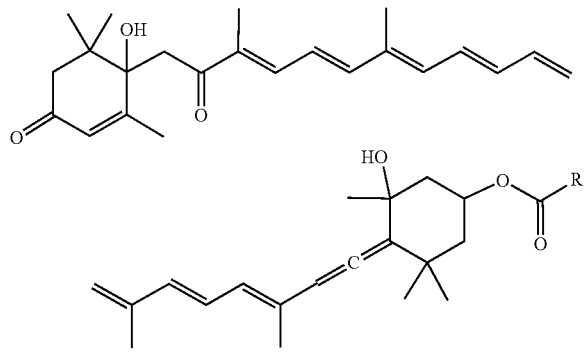

14 Claims, 1 Drawing Sheet

(56) References Cited

OTHER PUBLICATIONS

Akira Asai et al., "Biotransformation of Fucoxanthinol Into Amarouciaxanthin a in Mice and HEPG2 Cells: Formation and Cytotoxicity of Fucoxanthin Metabolites," Drug Metabolism and Disposition, Feb. 2004, pp. 205-211, vol. 32.
Koji Mikami et al., "Biosynthetic Pathway and Health Benefits of Fucoxanthin, an Algae-Specific Xanthophyll in Brown Seaweeds," Int J Mol Sci. Jul. 2013, pp. 13, 763-13, 781, vol. 14.
Minkyung Bae et al., "Health benefits of fucoxanthin in the prevention of chronic diseases," Biochim Biophys Acta Mol Cell Biol Lipids, Nov. 2020, 1865, 158618.
Yumiko Yamano et al., "Stereocontrolled First Total Syntheses of Amarouciaxanthin A and B," Organic Letters, Oct. 2013, pp. 5, 310-5, 313, vol. 15, No. 20.
Yoshiko Satomi, "Antitumor and Cancer-preventative Function of Fucoxanthin: A Marine Carotenoid," Anticancer Research, Apr. 2017, pp. 1, 557-1, 562, vol. 37, No. 4.
Juan Peng et al., "Fucoxanthin, a Marine Carotenoid Present in Brown Seaweeds and Diatoms: Metabolism and Bioactivities Relevant to Human Health," Marine Drugs, Oct. 2011, pp. 1, 806-1, 828, vol. 9, No. 10.
Hayato Maeda, "Nutraceutical Effects of Fucoxanthin for Obesity and Diabetes Therapy: A Review," Journal of Oleo Science, Jan. 2015, pp. 125-132, vol. 64, No. 2.
Han Xiao et al., "Advances in Studies on the Pharmacological Activities of Fucoxanthin," Marine Drugs, Dec. 2020, 18, 634.
Jingqian Su et al., "Fucoxanthin, a Marine Xanthophyll Isolated From Conticribra weissflogii ND-8: Preventive Anti-Inflammatory Effect in a Mouse Model of Sepsis," Frontiers in Pharmacology, Aug. 2019, vol. 10, Article 906.
Xiaoling Li et al., "Fucoxanthin attenuates LPS-induced acute lung injury via inhibition of the TLR4/MyD88 signaling axis," Aging, Dec. 2020, pp. 2, 655-2, 667, vol. 13, No. 2.
Yuan-Ping Yang et al., "Anti-inflammatory effect of fucoxanthin on dextran sulfate sodium-induced colitis in mice," Natural Product Research, Nov. 2018, pp. 1791-1795.
Jiawen Zheng et al., "Protective Effects of Fucoxanthin against Alcoholic Liver Injury by Activation of Nrf2-Mediated Antioxidant Defense and Inhibition of TLR4-Mediated Inflammation," Marine Drugs, Sep. 2019, 17, 552.
Xinjun Yang et al., "Assessment of the Therapeutic Effects of Fucoxanthin by Attenuating Inflammation in Ovalbumin-Induced Asthma in an Experimental Animal Model," Journal of Environmental Pathology, Toxicology and Oncology, Jan. 2019, pp. 229-238, 38(3).
Naoki Takatani et al., "Fucoxanthin inhibits hepatic oxidative stress, inflammation, and fibrosis in diet-induced nonalcoholic steatohepatitis model mice," Biochemical and Biophysical Research Communications, May 2020, pp. 305-310, 528.
Sun Young Ma et al., "Fucoxanthin inhibits profibrotic protein expression in vitro and attenuates bleomycin-induced lung fibrosis in vivo," European Journal of Pharmacology, Jun. 2017, pp. 199-207, 811.
Tomasz M. Karpinski et al., "Fucoxanthin—An Antibacterial Carotenoid," Antioxidants, Jul. 2019, 8, 239.
Lixun Hu et al., "Neuroprotective role of fucoxanthin against cerebral ischemic/reperfusion injury through activation of Nrf2/HO-1 signaling," Biomedicine & Pharmacotherapy, Oct. 2018, pp. 1, 484-1, 489, 106.
Rulin Wang et al., "Antiurolithiatic effect of Fucoxanthin on ethylene glycol-induced renal calculus in experimental rats," Journal of King Saud University—Science, Jan. 2020, pp. 1, 896-1, 901, 32.
Zulfiia Guvatova et al., "Protective effects of carotenoid fucoxanthin in fibroblasts cellular senescence," Mechanisms of Ageing and Development, May 2020, 189, 111260.
Shiu-Jau Chen et al., "Cytoprotective Potential of Fucoxanthin in Oxidative Stress-Induced Age-Related Macular Degeneration and Retinal Pigment Epithelial Cell Senescence In Vivo and In Vitro," Marine Drugs, Feb. 2021, 19, 114.
Liao Zhiyin et al., "Fucoxanthin rescues dexamethasone induced C2C12 myotubes atrophy," Biomedicine & Pharmacotherapy, Apr. 2021, 139, 111590.
Pamela J. Walsh et al., "The Osteogenic Potential of Brown Seaweed Extracts," Marine Drugs, Feb. 2019, 17, 141.
Chika Natsume et al., "Fucoxanthin Ameliorates Atopic Dermatitis Symptoms by Regulating Keratinocytes and Regulatory Innate Lymphoid Cells," Int J Mol Sci., Mar. 2020, 21, 2180.
Haoyue Yang et al., "Effect of Fucoxanthin Administration on Thyroid Gland Injury Induced by Cadmium in Mice," Biological Trace Element Research, Jul. 2020.
So Young Kang et al., "Antiaging Potential of Fucoxanthin Concentrate Derived from Phaeodactylum tricornutum," J Cosmet Sci., Mar. 2020, pp. 53-64, 71.
Yamano Yumiko et al., "Stereocontrolled First Total Syntheses of Amarouciaxanthin A and B," Organic Letters, Oct. 2013, pp. 5, 310-5, 313, vol. 15, No. 20.
International Search Report and Written Opinion for PCT/EP2022/070001, mailed Nov. 24, 2022.
Decision to Grant a European Patent for EP Application No. 21382644.9, mailed Nov. 3, 2023.
Extended European Search Report for EP Application No. 21382644.9, mailed Feb. 17, 2022.
Shiro Komba et al., "Fucoxanthin Derivatives: Synthesis and their Chemical Properties," Journal of Oleo Science, May 2015, pp. 1, 009-1, 018, vol. 64, No. 9.
First Office Action for China Application No. 202280035018.8, mailed Feb. 4, 2024.
Takashi Maoka, et al., New C37 Skeletal Carotenoid from the Clam, Paphia mabillis, J. Agric. Food Chem., Dec. 2008, vol. 56, No. 24, p. 12069-12072.
Takashi Hashimoto, et al., The distribution and accumulation of fucoxanthin and its metabolites are oral administration in mice, British Journal of Nutrition, Jan. 2009, vol. 102, No. 2, p. 242-248.
Statchi, Satsuma ark shell miso soup, [online], Dec. 6, 2005, [Retrieved Jun. 17, 2024], https://cookpad.com/recipe/229673.
Miyashita Kazuo, et al., Nutraceutical characteristics of the brown seaweed carotenoid fucoxanthin, Archives of Biochemistry and Biophysics, Jun. 15, 2020, vol. 686, Article No. 108364, p. 1-35.
Notice of Reasons for Refusal dated Jun. 25, 2024, in JP 2023579284.

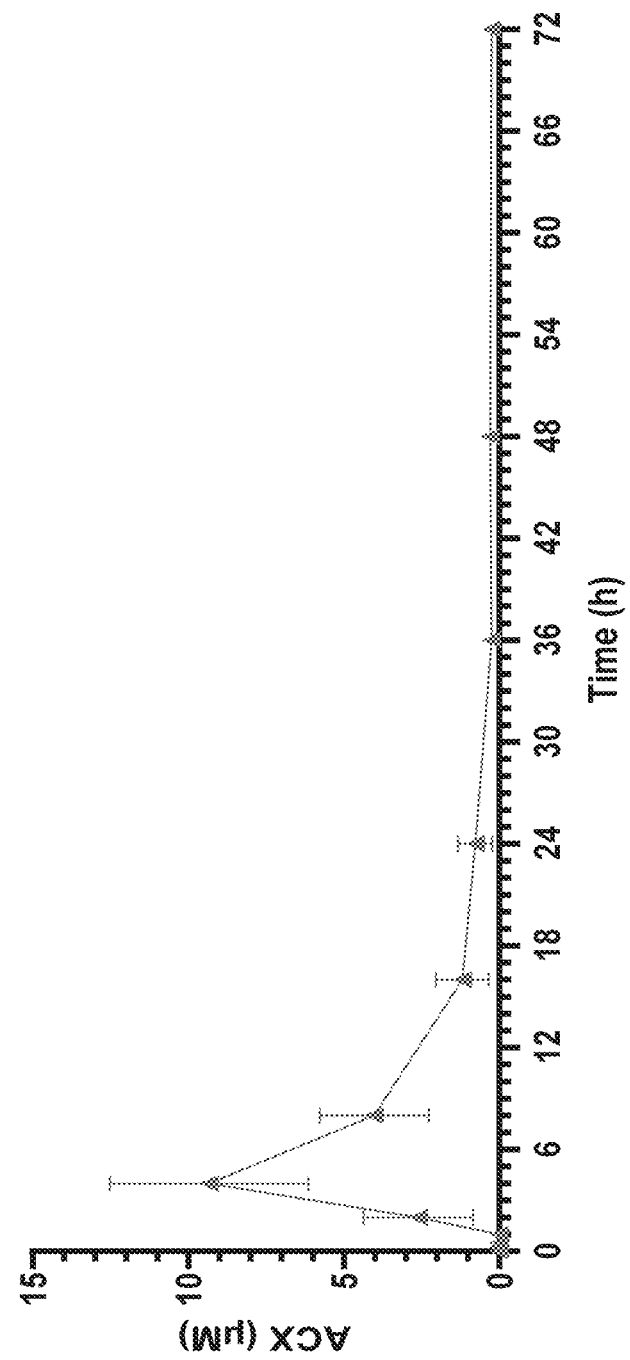

AMAROUCIAXANTHIN A ESTERS AND USES THEREOF

FIELD OF THE INVENTION

The invention relates to amarouciaxanthin A esters, their method of preparation, compositions comprising them as well as their medical and cosmetic uses.

BACKGROUND OF THE INVENTION

Amarouciaxanthin A (ACX) is a naturally occurring xanthophyll which was first isolated from *Amaroucium pliciferum* (J Nat Prod, 1985, 48, 606-613). It is one of the main metabolites of fucoxanthin in mice after oral administration and the postulated metabolism is deacetylation of fucoxanthin (FCX) into fucoxanthinol followed by rearrangement in the liver to ACX (Drug Metab Dispos, 2004, 32, 205-211).

It is well known in the literature the wide range of applications of fucoxanthin (FCX) such as an antioxidant, antiobesity, antidiabetic, anticarcinogenic among others (Int J Mol Sci, 2013, 14, 13763-13781, Biochim Biophys Acta Mol Cell Biol Lipids, 2020, 1865, 158618). On the other hand, only recently ACX has been reported to significantly inhibit hepatic oxidative stress, inflammation, and fibrosis in rodent models (Biochem Biophys Res Commun, 2020, 528, 305-310) which makes this compound a very promising candidate.

FCX is widely distributed in brown seaweeds, diatoms and dinoflagellates and it is commercially available from natural extracts. Unfortunately there are no direct sources to obtain ACX or its derivatives since it is present in nature in only small amounts. It has been previously obtained either from natural extracts after a tedious purification process or by a very long chemical synthesis with low total yield and the risk of not fully controlling its chiral centers (Org Lett, 2013, 15, 5310-5313).

Therefore, there is a need of ACX prodrugs which can be synthesized in good yields, with no isomerization of the chiral centers, and which directly transform into ACX after administration, without intermediate metabolites as occurs when administering FCX.

BRIEF DESCRIPTION OF THE INVENTION

The inventors have unexpectedly found that ACX esters, in particular the acetate ester, spontaneously transform into ACX and its cis-isomers in the body. This ester may be easily obtained from commercially available fucoxanthin by means of a one-pot single step synthesis with total conversions and no risk of isomerization of the chiral centers. Also, the acetate ester can be used as a precursor of ACX to obtain pure ACX, further ACX ester derivatives or other fucoxanthin metabolites.

Thus, in the first aspect, the invention relates to a compound of formula (I)

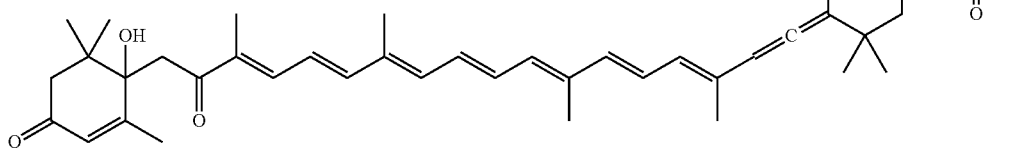

wherein R is selected from the group consisting of linear or branched $C_1$-$C_4$ alkyl, or a stereoisomer thereof.

In the second aspect, the invention relates to a process for preparing a compound as defined in the first aspect, which comprises:

a) reacting a compound of formula (II) or (IIa)

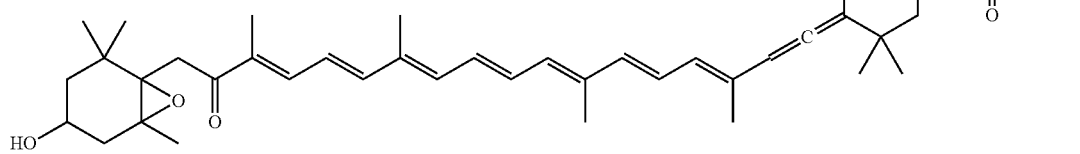

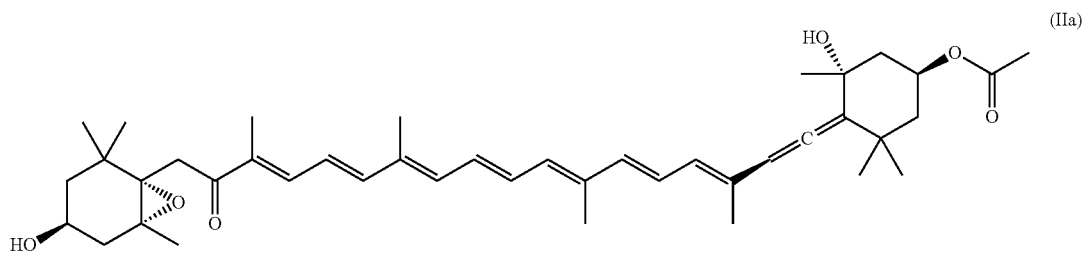

with an oxidant, preferably an oxidant selected from the group consisting of tetra-n-propylammonium perruthenate (TPAP) and 2-iodoxybenzoic acid (IBX) and optionally also in the presence of a co-oxidant, preferably N-methylmorpholine N-oxide (NMO), to give a compound of formula (III) or (IIIa)

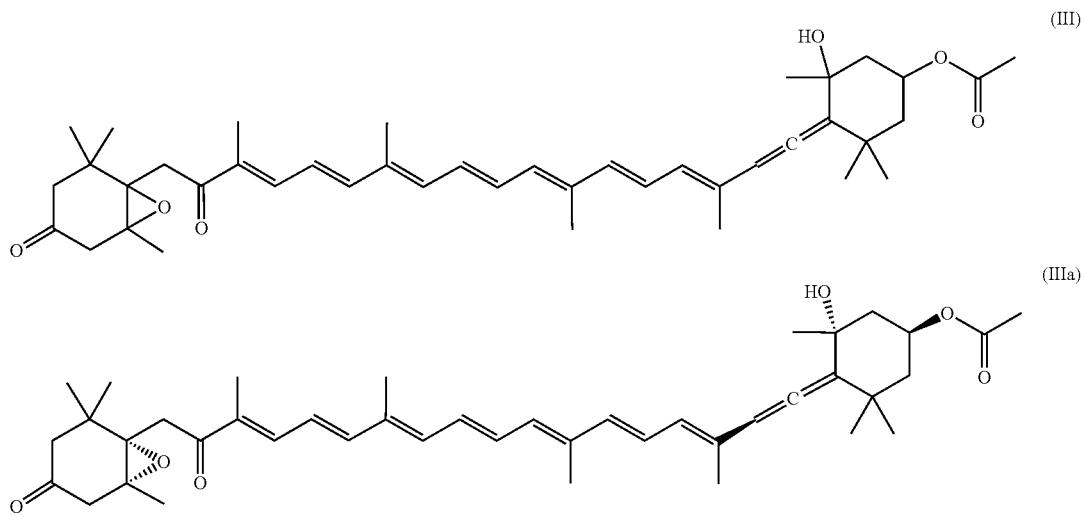

b) treating the compound of formula (III) or (IIIa) with SiO$_2$ in the presence of a base, preferably a base selected from the group consisting of N-methylmorpholine and triethylamine, to give a compound of formula (I) or (Ia) wherein R is methyl, and c) wherein if the compound of formula (I) or (Ia) R is a linear or branched C$_2$-C$_4$ alkyl, the process further comprises:

c1) converting the compound of formula (I) or (Ia) wherein R is methyl to a compound of formula (IV) or (IVa)

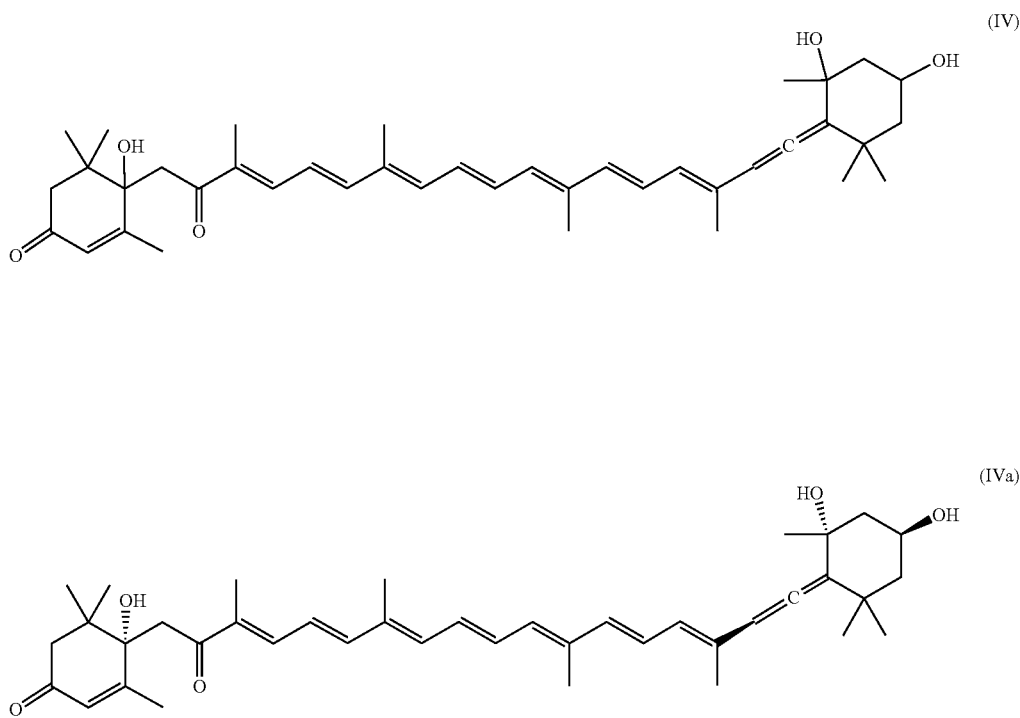

by treatment with an esterase, preferably a lipase, and
c2) esterification of the compound of formula (IV) or (IVa) with a carboxylic acid of formula (V)

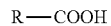
(V)

wherein R is a linear or branched $C_2$-$C_4$ alkyl, in the presence of a coupling agent, preferably a carbodiimide, more preferably a carbodiimide selected from the group consisting of dicyclohexylcarbodiimide (DDC), diisopropylcarbodiimide (DIC) and ethyl-(N',N'-dimethylamino)propylcarbodiimide (EDC) or a salt thereof, and in the presence of 4-(dimethylamino)pyridine (DMAP), to give a compound of formula (I) or (Ia)

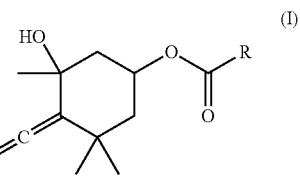

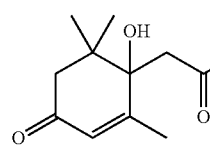

(I)

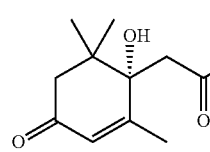

(Ia)

wherein R is selected from the group consisting of linear or branched $C_2$-$C_4$ alkyl.

The third aspect relates to the use of a compound according to the first aspect for the preparation of amarouciaxanthin A and/or a composition comprising amarouciaxanthin A and paracentrone.

The fourth aspect relates to a process for preparing amarouciaxanthin A comprising treating the compound according to the first aspect with an esterase, preferably a lipase.

The fifth aspect relates to a composition comprising a compound according to the first aspect and a compound of formula (VI), preferably of formula (VIa)

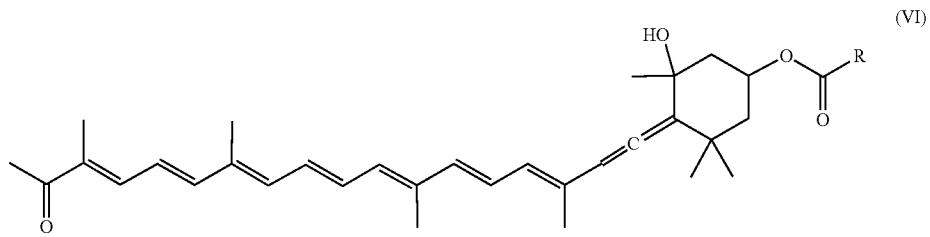
(VI)

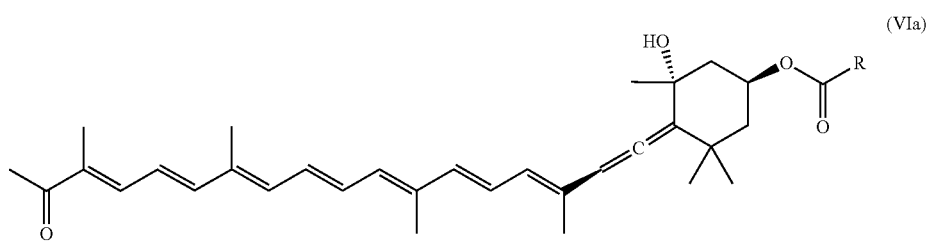
(VIa)

wherein R is selected from the group consisting of linear or branched $C_2$-$C_4$ alkyl, preferably methyl, preferably a compound of formula (VIa), preferably a compound of formula (VIa) wherein R is methyl.

The sixth aspect relates to a pharmaceutical composition comprising a compound according to the first aspect or a composition according to the fifth aspect.

The seventh aspect relates to a compound according to first aspect, a composition according to the fifth aspect or pharmaceutical composition according to the sixth aspect, for use in medicine.

The eighth aspect relates to a compound according to the first aspect, a composition according to the fifth aspect or pharmaceutical composition according to the sixth aspect, for use in the treatment and/or prevention of a disease selected form the group consisting of cancer, a cardiovascular disease, an intestinal flora imbalance, an inflammatory disease, an autoimmune disease, fibrosis, a bacterial infection, a neurological disease, a hyperuricemic-related disease, a senescence-related disorder, a lipid related disease, glucocorticoid induced muscle atrophy, a bone-related disease, an ocular disease, an angiogenic related disease, psoriasis, eczema, atopic dermatitis, and a thyroid-related disorder.

The ninth aspect relates to a food, a cosmeceutical, a nutraceutical, or a cosmetic composition comprising a compound according to the first aspect or a composition according to the fifth aspect.

The tenth aspect relates to a cosmetic method for preventing and/or decreasing cutaneous senescence and/or for ameliorating the cosmetic adverse effects of aging comprising administering the compound according to the first aspect, a composition according to the fifth aspect or the food, cosmeceutical, nutraceutical or cosmetic composition according to the ninth aspect, to a subject in need thereof.

DESCRIPTION OF THE FIGURES

FIG. 1 shows the plasma concentration of amarouciaxanthin A after oral delivery of amarouciaxanthin A acetate.

DETAILED DESCRIPTION OF THE INVENTION

Compounds of Formula (I)

The first aspect of the invention relates to a compound of formula (I)

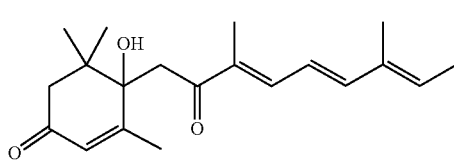
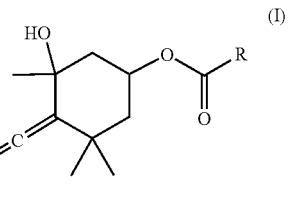

(I)

wherein R is selected from the group consisting of linear or branched $C_1$-$C_4$ alkyl, or a stereoisomer thereof.

The term "alkyl" refers to a straight or branched hydrocarbon chain radical consisting of carbon and hydrogen atoms, containing no unsaturation, having one to four carbon atoms, and which is attached to the rest of the molecule by a single bond, e. g., methyl, ethyl, n-propyl, iso-propyl, n-butyl, tert-butyl, iso-butyl, and sec-butyl. Preferably, the alkyl is methyl.

The term "stereoisomer" makes reference to compounds made up of the same atoms bonded by the same sequence of bonds but having different three-dimensional structures which are not interchangeable.

In a preferred embodiment, the compound of the invention is a compound of formula (Ia)

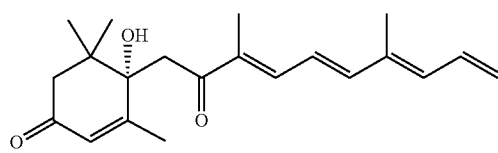
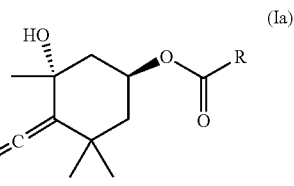

(Ia)

wherein R is as previously defined

In preferred embodiment, the compound of the invention is a compound of formula (I) wherein R is methyl.

In a more preferred embodiment, the compound of the invention is a compound of formula (Ia) wherein R is methyl, i.e. amarouciaxanthin A acetate.

Process for the Preparation of Compounds of Formula (I)

The second aspect of the invention relates to a process for preparing a compound as defined in the first aspect, which comprises:

a) reacting a compound of formula (II) or (IIa)

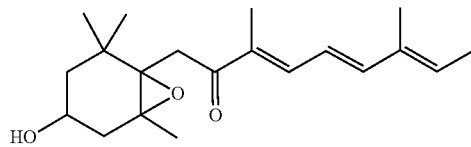
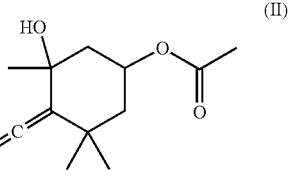

(II)

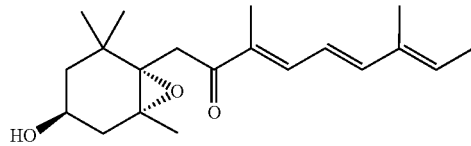
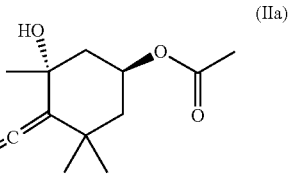

(IIa)

with an oxidant, preferably an oxidant selected from the group consisting of tetra-n-propylammonium perruthenate (TPAP) and 2-iodoxybenzoic acid (IBX) and optionally also in the presence of a co-oxidant, preferably N-methylmorpholine N-oxide (NMO), to give a compound of formula (III) or (IIIa)

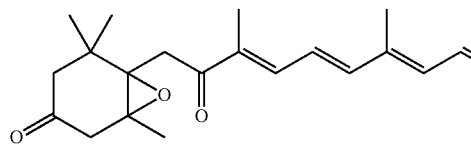
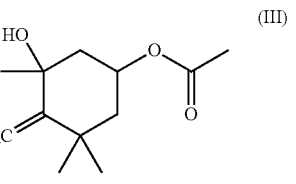

(III)

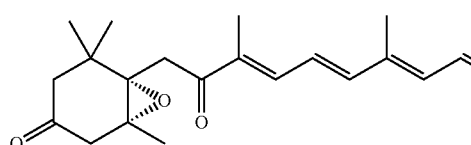
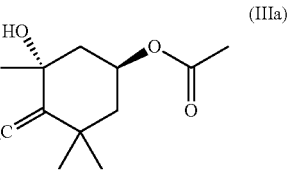

(IIIa)

b) treating the compound of formula (III) or (IIIa) with SiO$_2$ in the presence of a base, preferably a base selected from the group consisting of N-methylmorpholine and triethylamine, to give a compound of formula (I) or (Ia) wherein R is methyl, and c) wherein if the compound of formula (I) or (Ia) R is a linear or branched C$_2$-C$_4$ alkyl, the process further comprises:
c1) converting the compound of formula (I) or (Ia) wherein R is methyl to a compound of formula (IV) or (IVa)

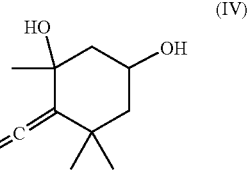
(IV)

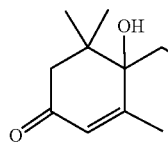

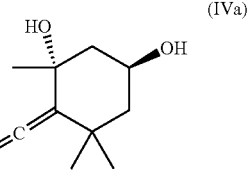
(IVa)

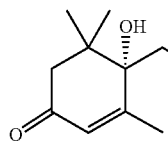

by treatment with an esterase, preferably a lipase, and
c2) esterification of the compound of formula (IV) or (IVa) with a carboxylic acid of formula (V)

$$R-COOH \quad (V)$$

wherein R is a linear or branched C$_2$-C$_4$ alkyl,
in the presence of a coupling agent, preferably a carbodiimide, more preferably a carbodiimide selected from the group consisting of dicyclohexylcarbodiimide (DDC), diisopropylcarbodiimide (DIC) and ethyl-(N',N'-dimethylamino)propylcarbodiimide (EDC) or a salt thereof, and in the presence of 4-(dimethylamino)pyridine (DMAP), to give a compound of formula (I) or (Ia)

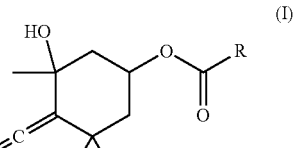
(I)

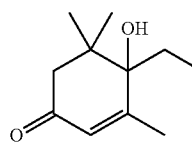

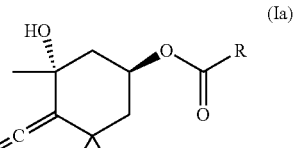
(Ia)

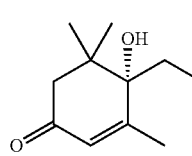

wherein R is selected from the group consisting of linear or branched $C_2$-$C_4$ alkyl.

When step a) is carried out with a compound of formula (II), a compound of formula (III) is obtained in this step, a compound of formula (I) wherein R is methyl is obtained in step b), a compound of formula (IV) is obtained in step c1) and a compound of formula (I) wherein R is $C_2$-$C_4$ alkyl is obtained in step c2).

When step a) is carried out with a compound of formula (IIa), a compound of formula (IIIa) is obtained in this step, a compound of formula (Ia) wherein R is methyl is obtained in step b), a compound of formula (IVa) is obtained in step c1) and a compound of formula (Ia) wherein R is $C_2$-$C_4$ alkyl is obtained in step c2).

The oxidant of step a) may be any suitable oxidant capable of providing the compound of formula (III) or (IIIa). Examples of oxidants are tetra-n-propylammonium perruthenate (TPAP) and 2-iodoxybenzoic acid (IBX), preferably TPAP.

Co-oxidants may also be used in step a). Examples and suitable co-oxidants are N-methylmorpholine N-oxide (NMO).

Preferably, step a) is carried out using TPAP as oxidant and NMO as co-oxidant.

The reaction of step a) is preferably carried out in an organic solvent such as dichloromethane, acetonitrile, acetone, methyl ethyl ketone, ethyl acetate, tetrahydrofuran or mixtures thereof, preferably dichloromethane.

The reaction of step a) is preferably carried out at a temperature in the range of 15° C. to 35° C.

The amount of oxidant used in step a) is preferably from 0.01 to 0.5 mol with respect to each mol of the compound of formula (II) or (IIa), more preferably from 0.05 to 0.2 mol.

When present, the amount of co-oxidant used in step a) is preferably from 1.5 to 5 mol with respect to each mol of the compound of formula (II) or (IIa), more preferably from 1.5 to 2.5 mol.

Step a) is preferably carried out with the removal of water. For example molecular sieves of 4 Å may be used in step a).

In another embodiment, step a) is carried out without the removal of water.

Preferably, step a) is carried out for 0.5 to 5 h.

Step a) provides a compound of formula (III) or (IIIa). When step a) is carried out with a compound of formula (II), a compound of formula (III) is obtained in this step. When step a) is carried out with a compound of formula (IIa), a compound of formula (IIIa) is obtained in this step.

The next step in the process is step b) of treating the compound of formula (III) or (IIIa) with $SiO_2$ in the presence of a base, preferably a base selected from the group consisting of N-methylmorpholine and triethylamine, to give a compound of formula (I) or (Ia) wherein R is methyl.

The compound of formula (III) or (IIIa) is obtained in step a).

The amount of $SiO_2$ used in step b) is preferably from 10 to 50 mol with respect to each mol of the compound of formula (II) or (IIa).

Step b) is carried out in the presence of a base. Examples of suitable bases are N-methylmorpholine, trimethylamine, N,N-diisopropylethylamine and mixtures thereof, preferably N-methylmorpholine.

The amount of base used in step b) is preferably from 0.1 to 5 mol with respect to each mol of the compound of formula (II) or (IIa).

In a particular embodiment, step a) is carried out in the presence of NMO as co-oxidant, providing N-methylmorpholine as a subproduct, which is then used as the base in step b).

Thus, in a particular embodiment, steps a) and b) are carried out one-pot.

The reaction of step b) is preferably carried out in an organic solvent such as dichloromethane, acetonitrile, acetone, methyl ethyl ketone, ethyl acetate, tetrahydrofuran or mixtures thereof, preferably dichloromethane.

The reaction of step b) is preferably carried out at a temperature in the range of 15° C. to 35° C.

Preferably, step b) is carried out for 0.5 to 24 h.

Step b) provides a compound of formula (I) or (Ia) wherein R is methyl. When step b) is carried out with a compound of formula (III), a compound of formula (I) wherein R is methyl is obtained in this step. When step b) is carried out with a compound of formula (IIIa), a compound of formula (Ia) is obtained in this step.

If the target compound of the process of the invention is a compound of formula (I) or (Ia) wherein R is methyl, step c) is not performed.

If the target compound of the process of the invention is a compound of formula (I) or (Ia) wherein R is a linear or branched $C_2$-$C_4$ alkyl, step c) is performed. Step c) comprises steps c1) and c2).

Step c1) is converting the compound of formula (I) or (Ia) wherein R is methyl to a compound of formula (IV) or (IVa)

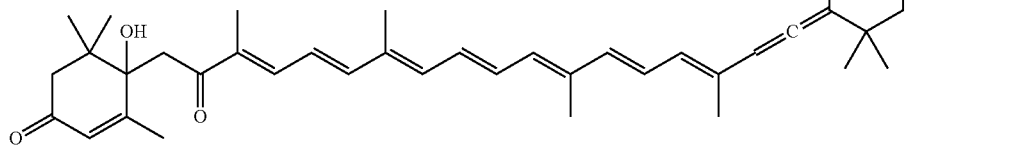

-continued

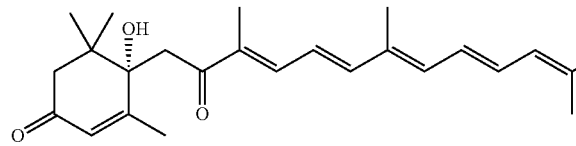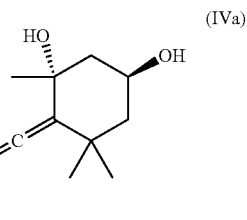

(IVa)

by treatment with an esterase, preferably a lipase.

The compound of formula (IV) or (IVa) is obtained in step b).

Any esterase capable of providing compound (IV) or (IVa) from a compound of formula (I) or (Ia), respectively, may be used. Examples of esterases are lipase and cholesterol esterase, preferably a lipase.

Step c1) is preferably carried out in the presence of an emulsifier such as sodium taurocholate, sodium dodecyl sulfate or a hydrate thereof.

Preferably, step c1) is carried out in an aqueous solvent, preferably at a pH of 6.5 to 7.5, more preferably, step c1) is carried out in phosphate-buffered saline solution (PBS).

The reaction of step c1) is preferably carried out at a temperature in the range of 30° C. to 45° C.

Preferably, step c1) is carried out for 2 to 24 h.

Step c1) provides a compound of formula (IV) or (IVa). When step c1) is carried out using a compound of formula (I), a compound of formula (IV) is obtained in this step. When step c1) is carried out using a compound of formula (Ia), a compound of formula (IVa) is obtained in this step.

The next step of the process of the invention is step c2) of esterification of the compound of formula (IV) or (IVa) with a carboxylic acid of formula (V)

wherein R is a linear or branched $C_2$-$C_4$ alkyl, in the presence of a coupling agent, preferably a carbodiimide, more preferably a carbodiimide selected from the group consisting of dicyclohexylcarbodiimide (DDC), diisopropylcarbodiimide (DIC) and ethyl-(N',N'-dimethylamino)propylcarbodiimide (EDC) or a salt thereof, and in the presence of 4-(dimethylamino)pyridine (DMAP), to give a compound of formula (I) or (Ia)

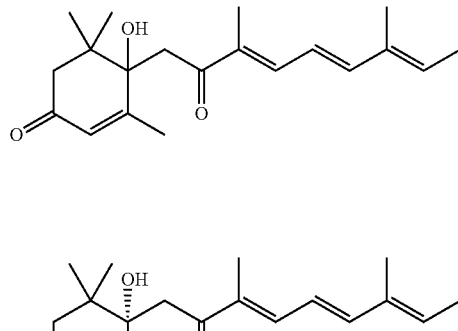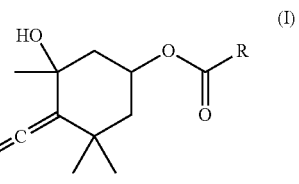

(I)

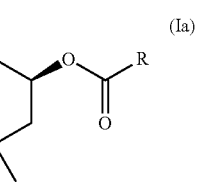

(Ia)

wherein R is selected from the group consisting of linear or branched $C_2$-$C_4$ alkyl.

The compound of formula (IV) or (IVa) is obtained in step c1).

The coupling agent used in step c2) may be any suitable coupling agent known in the art for esterification of a carboxylic acid with an alcohol. Examples of suitable coupling agents are carbodiimides, preferably dicyclohexylcarbodiimide (DDC), diisopropylcarbodiimide (DIC) and ethyl-(N',N'-dimethylamino)propylcarbodiimide (EDC) or a salt thereof. The esterification reaction of step c2) is carried out in the presence of DMAP.

Preferably, from 1 to 2 mol of coupling agent with respect to each mol of carboxylic acid (V) is used in step c2).

Preferably from 0.01 to 0.5 mol of DMAP with respect to each mol of carboxylic acid of formula (V) is used in step c2).

Preferably, from 1 to 2 mol of compound of formula (IV) or (IVa) with respect to each mol of carboxylic acid of formula (V) is used in step c2).

Preferably, step c2) is carried out in an organic solvent, such as dichloromethane, N,N-dimethylformamide or mixtures thereof.

The reaction of step c2) is preferably carried out at a temperature in the range of 0° C. to 30° C.

Preferably, step c2) is carried out for 1 to 15 h.

Step c2) provides a compound of formula (I) or (Ia) wherein R is selected from the group consisting of linear or branched $C_2$-$C_4$ alkyl. When step c2) is carried out using a compound of formula (IV), a compound of formula (I) wherein R is selected from the group consisting of linear or branched $C_2$-$C_4$ alkyl is obtained in this step. When step c2) is carried out using a compound of formula (IVa), a compound of formula (Ia) wherein R is selected from the group consisting of linear or branched $C_2$-$C_4$ alkyl is obtained in this step.

In a preferred embodiment, in the process of the invention:
the oxidant of step a) is TPAP,
step a) is carried out in the presence of a co-oxidant,
the co-oxidant in step a) is NMO; and/or
the base in step b) is N-methylmorpholine.

In another preferred embodiment, the step a) and/or b) of the process of the invention is carried out in the presence of water, in particular with more than 0.05 mol of water with respect to each mol of compound of formula (II) or (IIa). This provides a mixture of a compound of formula (I) or (Ia) and a compound of formula (VI) or (VIa)

The term "presence of water" refers to an amount of water of 0.1% by volume to 100% by volume, preferably 100%. This amount of water is determined with respect to the solvents present in the reaction medium without taking into account the water removed by any water removal agent.

The third aspect relates to the use of a compound according to the first aspect for the preparation of amarouciaxanthin A and/or a composition comprising amarouciaxanthin A and paracentrone.

The compound of formula (I) or (Ia) of the first aspect, preferably a compound of formula (Ia), preferably wherein R is methyl, may be used for the preparation of amarouciaxanthin A. Amarouciaxanthin A may be obtained, for example, by carrying out steps a), b) and c1) of the process of the invention, as described above.

The compound of formula (I) or (Ia) of the first aspect, preferably a compound of formula (Ia), preferably wherein R is methyl, may be used for the preparation of a compound of formula (VI) or (VIa) as described above, preferably a compound of formula (VIa), preferably wherein R is methyl (i.e. paracentrone acetate). The compound of formula (VI) or (VIa), preferably a compound of formula (VIa), preferably wherein R is methyl may be obtained, for example, by carrying out steps a) and/or b) of the process of the invention, as described above in the presence of water. This

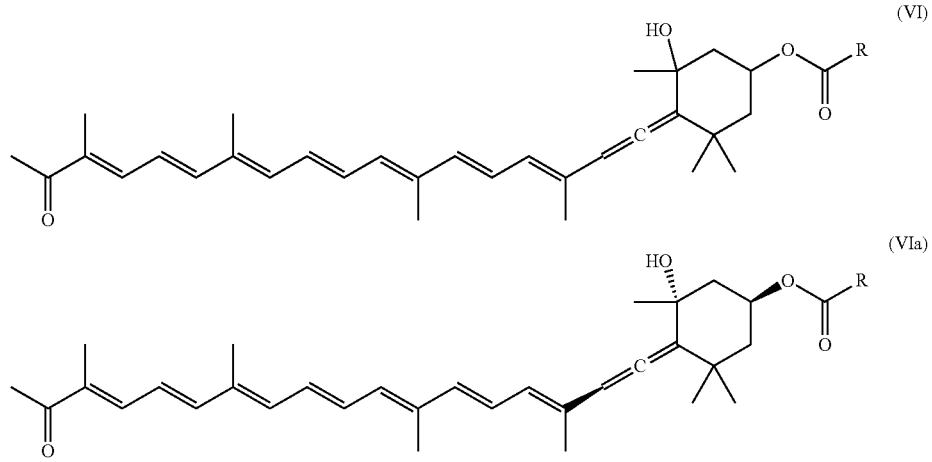

wherein R is selected from the group consisting of linear or branched $C_2$-$C_4$ alkyl, preferably methyl, preferably a compound of formula (VIa), preferably a compound of formula (VIa) wherein R is methyl.

Alternatively, a compound of formula (VI) or (VIa) can be obtained with heating the compound of formula (I) or (Ia) at 60 to 90° C. in the presence of water. In one embodiment, step a) is carried out in the presence of water. In another embodiment, step a) is carried without the presence of water. To avoid the presence of water in step a) a water removing agent, such as 4 Å molecular sieves, may be used. In another embodiment, step b) is carried out in the presence of water. In another embodiment, step b) is carried out without the presence of water. To avoid the presence of water in step a) a water removing agent, such as 4 Å molecular sieves, may be used. In another embodiment, both steps a) and b) are carried out in the presence of water. In another embodiment, both steps a) and b) are carried out without the presence of water. To avoid the presence of water in steps a) and b) a water removing agent, such as 4 Å molecular sieves, may be used.

process yields a mixture of a compound of formula (I) or (Ia) and a compound of formula (VI) or (VIa), preferably a mixture of a compound of formula (Ia) and a compound of formula (VIa), preferably wherein R is methyl.

The compound of formula (I) or (Ia) of the first aspect, preferably a compound of formula (Ia), preferably wherein R is methyl, may be used for the preparation of amarouciaxanthin A and paracentrone. Amarouciaxanthin A and paracentrone may be obtained, for example, by carrying out steps a), b) and c1) of the process of the invention, as described above, and wherein said steps a) and/or b) are carried out in the presence of water.

The fourth aspect relates to a process for preparing amarouciaxanthin A comprising treating the compound of formula (I) or (Ia) of the first aspect, preferably a compound of formula (Ia), preferably wherein R is methyl, with an esterase, preferably a lipase. The specific conditions have been described above with respect to steps a), b) and c1) of the process of the invention.

An additional aspect relates to a process for preparing paracentrone comprising treating the compound of formula (VI) or (VIa) described above, preferably a compound of formula (VIa), preferably wherein R is methyl, with an esterase, preferably a lipase. The specific conditions have been described above with respect to step c1) of the process of the invention.

Compositions

The fifth aspect relates to a composition comprising a compound of formula (I) or (Ia) according to the first aspect, preferably a compound of formula (Ia), preferably wherein R is methyl, and a compound of formula (VI) or (VIa) as described above, preferably a compound of formula (VIa), preferably wherein R is methyl.

In a particular embodiment, the amount of compound of formula (I) or (Ia) in the composition of the fifth aspect is from 10 to 99.9 wt % with respect to the total weight of the composition, preferably from 40 to 99 wt %.

In a particular embodiment, the amount of compound of formula (VI) or (VIa) in the composition of the fifth aspect if 1 to 60 wt % with respect to the total weight of the composition The sixth aspect relates to a pharmaceutical composition comprising a compound of formula (I) or (Ia) according to the first aspect, preferably a compound of formula (Ia), preferably wherein R is methyl, or a composition according to the fifth aspect.

The term "pharmaceutical composition", as used herein, relates to a composition comprising at least a combination provided by the present invention together with a pharmaceutically acceptable carrier.

The terms "pharmaceutically acceptable vehicle", "pharmaceutically acceptable carrier," "pharmaceutically acceptable diluent" or "pharmaceutically acceptable excipient", used interchangeably herein, refer to a non-toxic solid, semisolid or liquid filler, diluent, encapsulating material or formulation auxiliary of any conventional type. A pharmaceutically acceptable carrier is essentially non-toxic to recipients at the employed dosages and concentrations and is compatible with other ingredients of the formulation. The number and the nature of the pharmaceutically acceptable carriers depend on the desired administration form. The pharmaceutically acceptable carriers are known and may be prepared by methods well known in the art. They are involved in carrying or transporting the subject chemical from one organ, or portion of the body, to another organ, or portion of the body without excessive toxicity, irritation, allergic response, or other problem or complication, commensurate with a reasonable benefit/risk ratio. Each carrier must be "acceptable" in the sense of being compatible with the other ingredients of the formulation and not injurious to the patient. Some examples of materials which can serve as pharmaceutically-acceptable carriers include: (a) sugars (e.g. lactose, glucose and sucrose), (b) starches (e.g. corn starch and potato starch), (c) cellulose and its derivatives (e.g. sodium carboxymethyl cellulose, ethyl cellulose and cellulose acetate), (d) powdered tragacanth, (e) malt, (f) gelatin, (g) talc, (h) excipients (e.g. suppository waxes), (j) glycols (e.g. propylene glycol), (k) polyols (e.g. glycerin, sorbitol, mannitol and polyethylene glycol), (l) esters (e.g. ethyl oleate and ethyl laurate), (m) agar, (n) buffering agents (e.g. magnesium hydroxide and aluminum hydroxide), (o) alginic acid, (p) pyrogen-free water, (q) isotonic saline, (r) Ringer's solution, (s) ethyl alcohol, (t) phosphate buffer solutions and (u) other non-toxic compatible substances employed in pharmaceutical formulations. Wetting agents, emulsifiers and lubricants (e.g. sodium lauryl sulfate and magnesium stearate), as well as coloring agents, release agents, coating agents, sweetening, flavoring and perfuming agents, preservatives and antioxidants can also be present in the compositions. Examples of pharmaceutically-acceptable antioxidants include: (a) water soluble antioxidants (e.g. ascorbic acid, cysteine hydrochloride, sodium bisulfate, sodium metabisulfite or sodium sulfite), (b) oil-soluble antioxidants (e.g. ascorbyl palmitate, butylated hydroxyanisole (BHA), butylated hydroxytoluene (BHT), lecithin, propyl gallate or α-tocopherol), and (c) metal chelating agents (e.g. citric acid, ethylenediamine tetraacetic acid (EDTA), sorbitol, tartaric acid or phosphoric acid).

More preferably, the pharmaceutical product comprises a vehicle or carrier suitable for topical or oral administration.

Based on the particular mode of administration, the pharmaceutical product may be formulated into tablets, pills, capsules, sachets, granules, powders, suspensions, emulsions, anhydrous or hydrous topical formulations and solutions.

The pharmaceutical acceptable carriers or vehicles are well-known to those skilled in the art and are readily available to the public. It is preferred that the pharmaceutically acceptable carrier or vehicle be one which is chemically inert to the active formulation and each of its components and one which has no detrimental side effects or toxicity under the conditions of use.

In some embodiments, the pharmaceutical product is adapted as a delivery system for transporting the therapeutic agent orally, parenterally or intravenously into the circulatory system of a subject.

In cases other than intravenous administration, the composition can contain minor amounts of wetting or emulsifying agents, or pH buffering agents. The composition can be a liquid solution, suspension, emulsion, gel, polymer, or sustained release formulation. The composition can be formulated with traditional binders and carriers, as would be known in the art. Formulations can include standard carriers such as pharmaceutical grades of mannitol, lactose, starch, magnesium stearate, sodium saccharide, cellulose, magnesium carbonate, etc., inert carriers having well established functionality in the manufacture of pharmaceuticals. Various delivery systems are known and can be used to administer a therapeutic of the present invention including encapsulation in liposomes, microparticles, microcapsules and the like.

Where necessary, the combination or pharmaceutical composition of the invention, is comprised in a composition also including a solubilizing agent and a local anesthetic to ameliorate any pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water or saline. Where the combination is administered by injection, an ampule of sterile water for injection or saline can be provided so that the ingredients may be mixed prior to administration.

Formulations suitable for oral administration include liquid solutions, dissolved in diluents, such as water or saline; capsules, sachets, tablets, lozenges, each containing a predetermined amount of the combination of the invention; powders; suspensions in an appropriate liquid; and emulsions. Liquid dosage forms for oral administration may include emulsions, solutions, suspensions, syrups and elixirs pharmaceutically acceptable containing inert diluents commonly used in the technique, such as water. Those compositions may also comprise adjuvants such as wetting agents, emulsifying and suspending agents, and sweetening agents, flavoring and perfuming agents.

Solid dosage forms for oral administration may include conventional capsules, sustained release capsules, conventional tablets, sustained-release tablets, chewable tablets, sublingual tablets, effervescent tablets, pills, suspensions, powders, granules and gels. At these solid dosage forms, the active compounds can be mixed with at least one inert excipient such as sucrose, lactose or starch. Such dosage forms can also comprise, as in normal practice, additional substances other than inert diluents, e.g. lubricating agents such as magnesium stearate. In the case of capsules, tablets, effervescent tablets and pills, the dosage forms may also comprise buffering agents. Tablets and pills can be prepared with enteric coatings.

The parenteral formulations can be presented in unit-dose or multi-dose sealed containers, such as ampules and vials, and can be stored in freeze-dried (lyophilized) conditions requiring only the addition of the sterile liquid carrier, for example, water for injections, immediately prior to use.

The pharmaceutical composition of the invention can be administered by topical, transdermal or subcutaneous route. Illustrative examples of topical or transdermal administration include but are not limited to iontophoresis, sonophoresis, electroporation, mechanical pressure, osmotic pressure gradient, occlusive dressing, microinjections, needleless injections by means of pressure, microelectric patches and any combination thereof. In any case, the excipients will be chosen depending on the pharmaceutical dosage form selected.

Injectable preparations, for example, aqueous or oleaginous suspensions, sterile injectable may be formulated according with the technique known using suitable dispersing agents, wetting agents and/or suspending agents. Among the acceptable vehicles and solvents that can be used are water, Ringer's solution and isotonic sodium chloride solution. Sterile oils are also conventionally used as solvents or suspending media.

In a particular and preferred embodiment of the invention, the pharmaceutical composition of the invention is administered by topical route. For topical administration, the pharmaceutical compositions of the invention can be formulated as creams, gels, lotions, liquids, pomades, spray solutions, dispersions, solid bars, emulsions, microemulsions and similars which may be formulated according to conventional methods that use suitable excipients, such as, for example, emulsifiers, surfactants, thickening agents, coloring agents and combinations of two or more thereof.

Additionally, pharmaceutical compositions of the invention may be administered in the form of transdermal patches or iontophoresis devices. Suitable transdermal patches are well known by the person skilled in the art.

Several drug delivery systems are known and can be used to administer the combination of the invention, including, for example, encapsulation in liposomes, microbubbles, emulsions, microparticles, microcapsules, nanoparticles, nanocapsules and similars. The required dosage can be administered as a single unit or in a sustained release form. In a particular and preferred embodiment of the invention, the pharmaceutical composition is encapsulated in liposomes.

Sustainable-release forms and appropriate materials and methods for their preparation are well known in the state of the art. In one embodiment of the invention, the orally administrable form of a combination according to the invention is in a sustained release form further comprises at least one coating or matrix. The coating or sustained release matrix include, without limitation, natural polymers, semi-synthetic or synthetic water-insoluble, modified, waxes, fats, fatty alcohols, fatty acids, natural semisynthetic or synthetic plasticizers, or a combination of two or more of them. Enteric coatings may be applied using conventional processes known to experts in the art.

Another aspect relates to a food, a cosmeceutical, a nutraceutical, or a cosmetic composition comprising a compound according to the first aspect or a composition according to the fifth aspect.

As used herein, the term "food" is any substance or product of any nature, solid or liquid, natural or processed which due to its characteristics, applications, components, preparation and state of preservation, can usually or ideally be used for some of the following purposes: a) as normal nutrition for human beings or animals or as pleasurable foods; or b) as dietetic products, in special cases of human or animal food (feed). The term "feed" includes all the natural materials and finished products of any origin which, separately or conveniently mixed with one another, are suitable as animal food.

A ready-to-eat food is that which does not need to be diluted by means of an aqueous solution suitable for consumption for example. In principle, the ingredients present in a ready-to-eat food are balanced and there is no need to add additional ingredients to the food to make it ready to eat, such considered by a person skilled in the art. A concentrated food is that in which one or more ingredients are present at a higher concentration than in a ready-to-eat food, therefore for use it is necessary to dilute it by means of an aqueous solution suitable for consumption for example. Non-limiting, illustrative examples of foods provided by this invention include both dairy products and derivatives, for example, fermented milks, yoghurt, kephir, curd, cheeses, butters, ice creams, milk-based desserts, etc., and non-dairy products, such as baked products, cakes and pastries, cereals, chocolates, jams, juices, other fruit derivatives, oils and margarines, prepared dishes, etc.

As used herein, the term "cosmeceutical product" refers to a product suitable for use in the body or animal body comprising one or more cosmeceutical products (functional cosmetics, dermaceuticals or active cosmetics), i.e., topical hybrid products with cosmetic-pharmaceutical characteristics containing active ingredients having effect on user's skin, hair and/or nails, at higher and more effective concentrations, therefore they are located in an intermediate level between cosmetic and drug. Illustrative examples of cosmeceutical products include essential oils, ceramides, enzymes, minerals, peptides, vitamins, etc.

As used herein, the term "nutraceutical product" refers to a product suitable for use in human beings or animals, comprising one or more natural products with therapeutic action which provide a health benefit or have been associated with disease prevention or reduction, and it includes dietary supplements presented in a non-food matrix (e.g., capsules, powder, etc.) of a concentrated natural bioactive product usually present (or not) in the foods and which, when taken in a dose higher than that existing in those foods, exerts a favorable effect on health which is greater than effect which the normal food may have. Therefore, the term "nutraceutical product" includes isolated or purified food products as well as additives or food supplements which are generally presented in dosage forms normally used orally, for example, capsules, tablets, sachets, drinkable phials, etc.; such products provide a physiological benefit or protection against diseases, generally against chronic diseases. If desired, the nutraceutical product provided by the invention can contain, in addition to the xanthophylls, one or more nutraceuticals (products or substances associated with disease prevention or reduction), for example, flavonoids, omega-3 fatty acids, etc., and/or one or more prebiotics (non-digestible food ingredients which stimulate probiotic activity and/or growth), for example, oligofructose, pectin, inulin, galacto-oligosaccharides, lactulose, human milk oligosaccharides, dietary fiber, etc.

As used herein, the term "nutritional composition" of the present invention relates to a food product that beneficially affects one or more functions of the body, so as to provide better health and wellness. Accordingly, such a nutritional composition may be intended for the prevention and/or treatment of a disease or a disease causing factor. Therefore, the term "nutritional composition" of the present invention can be used as a synonym for functional food or foods for particular nutritional purposes, or medical food. A nutritional composition is similar to that of a conventional food and consumed as part of a normal diet appearance.

The term "cosmetic composition" or "personal care composition", as used herein, refers to a composition suitable for use in personal hygiene of human beings or animals, or in order to enhance the natural beauty or change the body appearance without affecting the structure or functions of the human or animal body, comprising one or more products providing such effects. If desired, the cosmetic composition provided by the invention can contain, in addition to the combination of the invention, one or more cosmetics or cosmetic products, i.e., substances or mixtures intended to be placed in contact with the external parts of the human or animal body (e.g., epidermis, hair system, nails, lips, etc.) or with the teeth and the buccal mucosa, for the exclusive or main purpose of cleaning them, perfuming them, changing their appearance, protecting them, keeping them in good condition or correcting body odors. Illustrative examples of cosmetically acceptable vehicles include the products contained in the INCI (International Nomenclature of Cosmetic Ingredients) list. Cosmetic or personal care compositions include products such as balms, pads, pomades, creams, etc. oils, surfactants, humectants, botanical extracts, vitamins, antioxidants, sunscreen agents, perfumes, preservatives, and the like. Illustrative examples of humectants, botanical extracts, vitamins, antioxidants and sunscreen agents.

The ingredients as described hereinabove are preferably provided in a cosmetic composition that may be formulated into a cream, gel, lotion, oil, ointment, powder, stick, cake, or other forms that can be topically applied. The resulting cosmetic composition may be in the form of a liquid, solid, semi-solid, dispersion, suspension, solution or emulsion, and it can be either aqueous-based or anhydrous. The cosmetic compositions of the invention may also be in the form of color cosmetic compositions, such as foundation makeup, mascara, lip color, blush, eye shadow, and the like. Certain other derivatives are lipophilic in nature and will more likely be found in the oil phase of the emulsion. The combination of the invention is preferably found in the water phase of the emulsion or encapsulated in an aqueous phase within liposomes.

The term "cosmetic effective amount", as used herein, relates to the sufficient amount of a compound (i.e of the combination of the invention) to provide the desired effect and it will generally be determined, by among other causes, the characteristics of the compound itself and the cosmetic effect to be achieved. The dosage for obtaining a cosmetic effective amount it will also depend on a range of factors, such as, for example, age, weight, sex or tolerance of the animal, preferably a mammal and more preferably human.

In a particular embodiment of the invention, the cosmetic composition of the invention is administered by topical route. Adequate formulations for topical administration of the composition of the invention are detailed in the context of the pharmaceutical compositions of the invention and equally apply to the cosmetic composition of the invention.

If desired, the cosmetic composition of the invention is incorporated in a fabric, a non-woven fabric or a medical device. Illustrative examples of said fabric, non-woven fabric or medical device include but are not limited to bandages, gauzes, t-shirts, panty hose, socks, underwear, girdles, gloves, diapers, sanitary napkins, dressings, bedspreads, towelettes, adhesive patches, non-adhesive patches, occlusive patches, microelectric patches and face masks.

Medical Uses

The utility of ACX for treating and/or preventing a variety of medical conditions have been described in the prior art, such as cancer (Satomi Y, Anticancer Res. 2017; 37(4): 1557-62; Méresse S et al., Int J Mol Sci. 2020 Dec. 4; 21(23); Peng J et al., Mar Drugs. 2011 Oct. 10; 9(10):1806-28), cardiovascular disease, hypertension, portal hypertension, pulmonary arterial hypertension, hyperglycemia, diabetes (Type 2), insulin resistance, as hepatoprotective and for lipid management related diseases (Peng J et al., Mar Drugs. 2011 Oct. 10; 9(10):1806-28), metabolic syndrome and diabetes prevention (Maeda H. J Oleo Sci. 2015 Jan. 20; 64(2):125-32), coronary atherosclerosis, rheumatoid arthritis and as anti-angiogenic (Méresse S et al., Int J Mol Sci. 2020 Dec. 4; 21(23)), intestinal flora imbalance, glaucoma, diabetic retinopathy, angiogenesis related diseases, hemorrhagic telangiectasia and psoriasis (Xiao H et al., Mar Drugs. 2020 Dec. 11; 18(12)), as anti-inflammatory, anaphylactic shock, sepsis, cytokine storm (Su et al., Front Pharmacol., 2019, DOI: 10.3389/fphar.2019.00906), lupus, sarcoidosis, chronic obstructive pulmonary disease (COPD), asthma, primary biliary cholangitis, sclerosing cholangitis, autoimmune hepatitis, inflammatory bowel disease, Crohn disease, multiple sclerosis, ulcerative colitis (Li X et al., Aging (Albany NY). 2021; 13:2655-2667; Yang Y P et al., Nat Prod Res. 2020 June; 34(12):1791-1795; Zheng J et al., Mar Drugs. 2019; 17(10):552; Yang X et al., J Environ Pathol Toxicol Oncol. 2019; 38(3):229-238; Takatani N et al., Biochem Biophys Res Commun. 2020 Jul. 23; 528(2) 305-310; Su et al., Front Pharmacol., 2019, DOI: 10.3389/fphar.2019.00906), fibrosis (Xiao H et al., Mar Drugs. 2020 Dec. 11; 18(12); Ma S Y et al. Eur J Pharmacol. 2017 Sep. 15; 811:199-207), as antibacterial (Karpiński T M, Adamczak A. Fucoxanthin—An Antibacterial Carotenoid. Antioxidants (Basel). 2019 Jul. 24; 8(8)), as neuroprotective agent (Hu L et al. Biomed Pharmacother. 2018 October; 106:1484-9), gout and kidney stones (Wang et al., Journal of King Saud University—Science. 2020 April; 32(3) 1896-1901), senescence-associated disorders (Guvatova Z et al., Mech Ageing Dev. 2020 July; 189:111260; Chen, S.-J. et al., Mar. Drugs 2021, 19, 114), glucocorticoid induced muscle atrophy (Zhiyin L et al. Biomed Pharmacother. 2021 Apr. 14; 139:111590), bone health (Walsh P J et al. Mar Drugs. 2019 Feb. 28; 17(3)), age related macular degeneration (Chen S-J et al. Mar Drugs. 2021 Feb. 18; 19(2)), eczema, atopic dermatitis and itch (Natsume C et al. Int J Mol Sci. 2020 Mar. 22; 21(6)) and thyroid-related disorders (Yang H et al., Biol Trace Elem Res. 2021 May; 199(5):1877-1884).

Moreover, ACX esters of formula (I) or (Ia) are prodrugs of ACX, which are spontaneously transformed into ACX and its cis-isomer in the body. Thus, the esters of the present invention are suitable for the treatment and prevention of the same diseases as reported for ACX.

Thus, in another aspect, the invention relates to a compound of formula (I) or (Ia) according to first aspect, a composition according to the fifth aspect or pharmaceutical composition according to the sixth aspect, for use in medicine.

In another aspect, the invention relates to a compound of formula (I) or (Ia) according to the first aspect, a composition according to the fifth aspect or pharmaceutical composition according to the sixth aspect, for use in the treatment and/or prevention of a disease selected form the group consisting of cancer, a cardiovascular disease, an intestinal flora imbalance, an inflammatory disease, an autoimmune disease, fibrosis, a bacterial infection, a neurological disease, a hyperuricemic-related disease, a senescence-related disorder, a lipid related disease, glucocorticoid induced muscle atrophy, a bone-related disease, an ocular disease, an angiogenic related disease, psoriasis, eczema, atopic dermatitis, and a thyroid-related disorder.

In another aspect, the invention relates to the use of a compound of formula (I) or (Ia) according to the first aspect, a composition according to the fifth aspect or pharmaceutical composition according to the sixth aspect, in the manufacture of a medicament for the treatment and/or prevention of a disease selected form the group consisting of cancer, a cardiovascular disease, an intestinal flora imbalance, an inflammatory disease, an autoimmune disease, fibrosis, a bacterial infection, a neurological disease, a hyperuricemic-related disease, a senescence-related disorder, a lipid related disease, glucocorticoid induced muscle atrophy, a bone-related disease, an ocular disease, an angiogenic related disease, psoriasis, eczema, atopic dermatitis, and a thyroid-related disorder.

In a further aspect, the invention relates to a method of treatment and/or prevention of a disease selected form the group consisting of cancer, a cardiovascular disease, an intestinal flora imbalance, an inflammatory disease, an autoimmune disease, fibrosis, a bacterial infection, a neurological disease, a hyperuricemic-related disease, a senescence-related disorder, a lipid related disease, glucocorticoid induced muscle atrophy, a bone-related disease, an ocular disease, an angiogenic related disease, psoriasis, eczema, atopic dermatitis, and a thyroid-related disorder, comprising administering to a subject in need thereof a compound of formula (I) or (Ia) according to the first aspect, a composition according to the fifth aspect or pharmaceutical composition according to the sixth aspect.

The term "prevention", "preventing" or "prevent", as used herein, relates to the administration of a combination according to the invention or of a medicament comprising said combination to a subject who has not been diagnosed as possibly having the disease, but who would normally be expected to develop said disease or be at increased risk for said disease. The prevention intends to avoid the appearance of said disease. The prevention may be complete (e.g. the total absence of a disease). The prevention may also be partial, such that for example the occurrence of a disease in a subject is less than that which would have occurred without the administration of the composition of the present invention. Prevention also refers to reduced susceptibility to a clinical condition.

The term "treatment", as used herein, refers to any type of therapy, which is aimed at terminating, preventing, ameliorating or reducing the susceptibility to a clinical condition as described herein. In a preferred embodiment, the term treatment relates to prophylactic treatment (i.e. a therapy to reduce the susceptibility to a clinical condition), of a disorder or a condition as defined herein. Thus, "treatment," "treating," and their equivalent terms refer to obtaining a desired pharmacologic or physiologic effect, covering any treatment of a pathological condition or disorder in a mammal, including a human. The effect may be prophylactic in terms of completely or partially preventing a disorder or symptom thereof and/or may be therapeutic in terms of a partial or complete cure for a disorder and/or adverse effect attributable to the disorder. That is, "treatment" includes (1) preventing the disorder from occurring or recurring in a subject, (2) inhibiting the disorder, such as arresting its development, (3) stopping or terminating the disorder or, at least, symptoms associated therewith, so that the host no longer suffers from the disorder or its symptoms, such as causing regression of the disorder or its symptoms, for example, by restoring or repairing a lost, missing or defective function, or stimulating an inefficient process, or (4) relieving, alleviating, or ameliorating the disorder, or symptoms associated therewith, where ameliorating is used in a broad sense to refer to at least a reduction in the magnitude of a parameter.

The term "cancer" as used herein, refers to a disease characterized by uncontrolled cell division (or by an increase of survival or apoptosis resistance) and by the ability of said cells to invade other neighbouring tissues (invasion) and spread to other areas of the body where the cells are not normally located (metastasis) through the lymphatic and blood vessels, circulate through the bloodstream, and then invade normal tissues elsewhere in the body. Depending on whether or not they can spread by invasion and metastasis, tumours are classified as being either benign or malignant: benign tumours are tumours that cannot spread by invasion or metastasis, i.e., they only grow locally; whereas malignant tumours are tumours that are capable of spreading by invasion and metastasis. As used herein, the term cancer includes, but is not limited to, the following types of cancer: breast cancer; biliary tract cancer; bladder cancer; brain cancer including glioblastomas, in particular glioblastoma multiforme, and medulloblastomas; cervical cancer; head and neck carcinoma; choriocarcinoma; colon cancer, colorectal cancer; endometrial cancer; esophageal cancer; gastric cancer; hematological neoplasms including acute lymphocytic and myelogenous leukemia; T-cell acute lymphoblastic leukemia/lymphoma; hairy cell leukemia; chronic myelogenous leukemia, multiple myeloma; AIDS-associated leukemias and adult T-cell leukemia/lymphoma; intraepithelial neoplasms including Bowen's disease and Paget's disease; liver cancer, hepatoma; lung cancer, pleural mesothelioma; lymphomas including Hodgkin's disease and lymphocytic lymphomas; neuroblastomas; oral cancer including squamous cell carcinoma; parotid gland cancer; ovarian cancer including those arising from epithelial cells, stromal cells, germ cells and mesenchymal cells; pancreatic cancer; prostate cancer; kidney cancer, suprarenal cancer; rectal cancer; sarcomas including leiomyosarcoma, rhabdomyosarcoma, liposarcoma, fibrosarcoma, and osteosarcoma; skin cancer including melanoma, Merkel cell carcinoma, Kaposi's sarcoma, basal cell carcinoma, and squamous cell cancer; cervix cancer, endometrial cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; and renal cancer including adenocarcinoma and Wilms tumor. Other cancers will-be known to one of ordinary skill. In a particular embodiment, the cancer is as gastric, duodenal, liver, hematologic, breast, glioma, bladder, pancreatic, prostate, colorectal, cervical, nasopharyngeal, lung, kidney, metastasis, melanoma, sarcoma, neural, or skin cancer.

In a particular embodiment, the cardiovascular disease is hypertension, portal hypertension, pulmonary arterial hypertension, hyperglycemia, type 2 diabetes, insulin resistance, metabolic syndrome or coronary atherosclerosis.

In a particular embodiment, the inflammatory disease is anaphylactic shock, sepsis or cytokine storm.

In a particular embodiment, the autoimmune diseases is lupus, sarcoidosis, chronic obstructive pulmonary disease, asthma, primary biliary cholangitis, sclerosing cholangitis, autoimmune hepatitis, inflammatory bowel disease, Crohn's disease, multiple sclerosis and ulcerative colitis.

"Fibrosis" as used herein relates to is the formation of excess fibrous connective tissue in an organ or tissue in a reparative or reactive process. Although fibrosis may be a benign state, the present invention relates preferably to fibrosis in a pathological state. In a particular embodiment, the fibrosis is liver fibrosis, renal fibrosis, lung fibrosis, myocardial fibrosis, interstitial fibrosis, IGG4-related fibrosis, sclerodermia or retroperitoneal fibrosis.

In a particular embodiment, the neurological disease is Parkinson's disease, Alzheimer's disease, dementia, depression or cerebral ischemia.

In a particular embodiment, the hyperuricemic-related disease is rheumatoid arthritis, gout or kidney stones.

In a particular embodiment, the lipid related disease is obesity, cholesterol, triglyceridaemia, non-alcoholic steatohepatitis or non-alcoholic fatty liver disease.

In a particular embodiment, the bone related diseases is bone loss.

In a particular embodiment, the ocular disease, is as glaucoma, diabetic retinopathy or age related macular degeneration.

In a particular embodiment, the angiogenesis related disease is hemorrhagic telangiectasia.

Cosmetic Methods

The utility of compounds of ACX in preventing and/or decreasing cutaneous senescence and/or for ameliorating the cosmetic adverse effects of aging have been described in the prior art (Peng J et al. Mar Drugs. 2011 Oct. 10; 9(10):1806-28; Kang S Y et al. J Cosmet Sci. 2020; 71(2):53-64.). As previously explained, ACX esters of formula (I) or (Ia) are spontaneously transformed into ACX and its cis-isomer in the body. Thus, the esters of the present invention are suitable for their use in the same cosmetic methods as reported for ACX.

Thus, in another aspect, the invention relates to a cosmetic method for preventing and/or decreasing cutaneous senescence and/or for ameliorating the cosmetic adverse effects of aging comprising administering the compound of formula (I) or (Ia), preferably of formula (Ia), preferably wherein R is methyl, according to the first aspect, a composition according to the fifth aspect or the food, cosmeceutical, nutraceutical or cosmetic composition according to the ninth aspect, to a subject in need thereof.

As used herein, the term "cosmetic method" relates to a method used to enhance the appearance of the skin in a subject. Cosmetic compositions used in the cosmetic method of the invention include skin-care creams, lotions, powders, lipsticks, eye and facial makeup, towelettes, gels, deodorants, hand sanitizer, baby products, bath oils, bubble baths, bath salts, butters and many other types of products.

Skin aging is a multi-factorial process that affects nearly every aspect of its biology and function; it is driven by both intrinsic (e.g., time, genetic factors, hormones) and extrinsic (e.g., UV exposure, pollution, cigarette smoke) factors. Skin aging is also produced by senescence.

Cellular senescence is a growth arrest that occurs as a result of different damaging stimuli, including DNA damage, telomere shortening and dysfunction or oncogenic stress. Senescent cells exert a pleotropic effect on development, tissue aging and regeneration, inflammation, wound healing and tumor suppression. Senescent cells are characterized by their inability to proliferate, resistance to apoptosis, and secretion of factors that promote inflammation and tissue deterioration.

Senescent keratinocytes and fibroblasts appear to accumulate with age in human skin. Moreover, senescent cells express genes that have long-range, pleiotropic effects-degradative enzymes, growth factors, and inflammatory cytokines.

"Cosmetic adverse effects of aging", as used herein relates to characteristics of intrinsic or chronological aging and include as a way of illustrative non limitative visible signs such as thin and dry skin, fine wrinkles, decreased elasticity, aberrant pigmentation, hair graying and hair loss.

"Cutaneous senescence", as used herein relates to means the state of growing old and particularly damage to the epidermal cells of human skin which results from partial damage or complete destruction of the cells, conversion of imide bonds to amide bonds in collagen and/or elastin caused by toxic byproducts of oxygen metabolism, free-radical pathology mechanisms or by photo-damage and generalized aging.

The cosmetic method of the invention is intended to decrease epidermal cell and thereby cutaneous senescence in a human by reducing or inhibiting senescence, including one or more affects such as reversing photo-damage or other regenerative effects, such as increasing underlying skin vascularity, increasing the rate of cellular replication and desquamation producing a more youthful appearance, increasing collagen synthesis and homogeneity, delaying cutaneous atrophy and thinning of epidermis and dermis, and the like.

The combination of the invention may be administered in a cosmetic effective amount. The term "cosmetic effective amount", as used herein, relates to the sufficient amount of a compound or composition of the invention to provide the desired effect and it will generally be determined, by among other causes, the characteristics of the compound itself and the cosmetic effect to be achieved. The dosage for obtaining a cosmetic effective amount it will also depend on a range of factors, such as, for example, age, weight, sex or tolerance of the animal, preferably a mammal and more preferably human.

In a particular and preferred embodiment of the cosmetic method of the invention, the cosmetic composition of the invention is administered by topical route. Adequate formulations for topical administration of the combination of the invention have been detailed in the context of the cosmetic compositions of the invention and equally apply to the cosmetic method of the invention.

If desired, the cosmetic composition of the invention is incorporated in a fabric, a non-woven fabric or a medical device. Illustrative examples of said fabric, non-woven fabric or medical device include but are not limited to bandages, gauzes, t-shirts, panty hose, socks, underwear, girdles, gloves, diapers, sanitary napkins, dressings, bedspreads, towelettes, adhesive patches, non-adhesive patches, occlusive patches, microelectric patches and face masks.

The following examples represent specific embodiments of the present invention. They do not intend to limit in any way the scope of the invention defined in the present description.

EXAMPLES

Analytical Methods
Nuclear Magnetic Resonance (NMR)

NMR spectra were acquired on a Varian 400 MHz or a 500 MHz instrument. 1H chemical shifts are quoted relative to deuterated solvent.

Example 1. Synthesis of Amarouciaxanthin A Acetate

Fucoxanthin (1 eq), NMO monohydrate (2 eq) and freshly dried 4 Å molecular sieves are dissolved with dichloromethane (DCM). TPAP (0.12 eq) is added at room temperature. When the reaction reaches complete conversion (>97%), $SiO_2$ (30 eq) is added to the reaction. The reaction is stirred at room temperature until complete conversion. The reaction is filtered to remove the $SiO_2$. The filtrate is washed with aqueous 5% $Na_2S_2O_3$. The organic layer is washed twice with brine, dried with $Na_2SO_4$, filtered and evaporated to dryness. The residue is dried using high-vacuum to obtain the desired compound as a red solid.

$^1$H-NMR (400 MHz, $CDCl_3$) δ 7.10 (d, J=10.9 Hz, 1H), 6.83-6.50 (m, 5H), 6.45 (d, J=11.6 Hz, 1H), 6.35 (d, J=15.0 Hz, 1H), 6.27 (d, J=11.7 Hz, 1H), 6.13 (d, J=11.5 Hz, 1H), 6.05 (s, 1H), 5.84 (s, 2H), 5.44-5.33 (m, 1H), 3.05 (d, J=15.0

Hz, 1H), 2.92 (d, J=15.0 Hz, 1H), 2.47 (d, J=18.1 Hz, 1H), 2.38-2.24 (m, 2H), 2.04 (s, 3H), 1.99 (m, 7H), 1.95 (s, 3H), 1.90 (d, J=1.0 Hz, 3H), 1.81 (s, 3H), 1.51 (t, J=12.2 Hz, 1H), 1.40 (m, 8H), 1.14-1.02 (m, 9H).

Example 2. Synthesis of Paracentrone Acetate

Amarouciaxanthin A acetate is mixed with water and heated to 70° C. Once the reaction does not evolve, it is cooled down and extracted with dichloromethane. The organic layer is dried, filtered and evaporated to dryness. The resulting residue is purified by $SiO_2$ column chromatography to obtain the desired compound as a brown solid.

Paracentrone acetate: $^1$H-NMR (500 MHz, $CDCl_3$) δ 7.14 (dd, J=10.7, 1.2 Hz, 1H), 6.77-6.53 (m, 5H), 6.42-6.30 (m, 2H), 6.26 (d, J=11.5 Hz, 1H), 6.12 (dd, J=11.4, 1.0 Hz, 1H), 6.06 (d, J=7.2 Hz, 1H), 5.38 (m, 1H), 2.36 (s, 3H), 2.31-2.25 (m, 1H), 2.03 (s, 3H), 2.02-1.96 (m, 6H), 1.93 (d, J=0.9 Hz, 3H), 1.81 (t, J=3.6 Hz, 3H), 1.50 (m, 1H), 1.44-1.39 (m, 1H), 1.36 (d, J=15.3 Hz, 6H), 1.09-1.03 (m, 3H).

Example 3. Synthesis of Amarouciaxanthin A Acetate Using Different Oxidants

The same procedure of example 1 was carried out but replacing TPAP and NMO with IBX, Dess-Martin periodinane and Swern oxidation. The results are gathered in the table table below:

| Reagent | Oxidized fucoxanthin | One pot $SiO_2$ addition |
|---|---|---|
| IBX | 100% conversion | Mixture oxidized fucoxanthin + desired compound |
| Dess-Martin periodinane | 55% conversion | — |
| Swern oxidation | 10% conversion | — |
| TPAP | 100% conversion | 100% conversion |

Example 4. Synthesis of Amarouciaxanthin A

Amarouciaxanthin A acetate (1 eq) and sodium taurocholate (30 eq) are dissolved in MeOH. The solvent is evaporated to dryness. The residue is dissolved in phosphate-buffered saline (PBS, pH 7) and lipase (1340 U/mg compound) is added. The reaction is shaken at 37° C. until maximum conversion (aprox 80%). The reaction is quenched with MeOH and extracted with $Et_2O$ and brine. The aqueous layer is extracted with $Et_2O$ until no colour is observed in the organic layer. The combined organic layers are dried, filtered and evaporated to dryness. The residue is purified by $SiO_2$ column chromatography and amarouciaxanthin A was obtained as a red solid and the unreacted amarouciaxanthin A acetate is recovered.

$^1$H-NMR (500 MHz, acetone) δ 7.53 (dd, J=10.8, 1.1 Hz, 1H), 6.93-6.81 (m, 2H), 6.80-6.67 (m, 3H), 6.52 (d, J=11.6 Hz, 1H), 6.36 (dd, J=17.7, 13.4 Hz, 2H), 6.16 (dd, J=11.4, 1.0 Hz, 1H), 6.02 (s, 1H), 5.91 (s, 1H), 5.74-5.69 (m, 1H), 4.28-4.17 (m, 1H), 3.61 (d, J=1.6 Hz, 1H), 3.48 (d, J=5.1 Hz, 1H), 3.21 (q, J=15.5 Hz, 2H), 2.80 (d, J=1.6 Hz, 3H), 2.78-2.75 (m, 1H), 2.62 (d, J=17.6 Hz, 1H), 2.21-2.11 (m, 2H), peaks under acetone, 2.02 (s, 2H), 1.99 (s, 2H), 1.94 (t, J=3.3 Hz, 2H), 1.91 (m, 1H), 1.89-1.83 (m, 5H), 1.40-1.24 (m, 7H), 1.07-0.98 (m, 6H).

Example 5. Conversion of Amarouciaxanthin A Acetate to Amarouciaxanthin after Oral Absorption Immunocompetent mice from the strain Hsd:ICR (CD-1) (females, 6-7 weeks old from ENVIGO), were housed under sterile conditions at a constant temperature of 20-22° C. and relative humidity (45-65%) under daily cycles of light/darkness (12 hours). Sterilized water and food were available ad libitum.

Amarouciaxanthin A acetate (ACX-Ac) was dissolved at 1 mg/mL in a suitable vehicle and sterilized by filtration. Animals were weighted before the assay to determine the appropriate dispensing volume at 10 mL/kg. Formulation was administered once, intragastrically, at 10 mg/kg. Blood was collected at different time points, as stated in Table 1. It was extracted either through the facial vein or by intracardiac puncture (end points), on recipients containing 5 μL of 0.5 M EDTA.

Blood samples were analyzed by HPLC-MS/MS following proprietary analytical methods and the concentration of ACX in each sample was determined. A noncompartmental pharmacokinetic analysis was carried out using individual plasma concentrations versus sampling times by means of the PKPlus® software version 2.0 (Simulations Plus, Lancaster, CA 93534, USA).

TABLE 1

Treatment groups in the ACX-Ac oral kinetic assay.

| Group | Number of animals | Blood extraction |
|---|---|---|
| 1 | 3 | 2 min, 8 h |
| 2 | 3 | 30 min, 24 h |
| 3 | 3 | 2 h, 48 h |
| 4 | 3 | 4 h, 72 h |
| 5 | 3 | 15 min, 16 h |
| 6 | 3 | 1 h, 36 h |

ACX-Ac was not detected in plasma samples when administered orally. The absorption of ACX was subsequently analyzed (FIG. 1). The estimated maximum observed plasma concentration (Cmax) was determined to be 9.35 μM; while the area under the concentration-time curve (AUCt) was calculated to be 80.59 μM·h.

The invention claimed is:

1. A compound of formula (I)

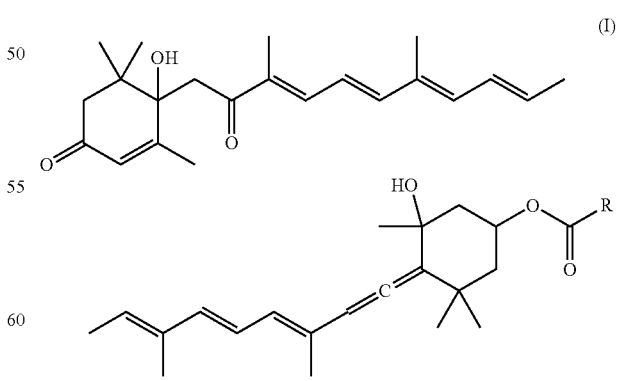

wherein R is selected from the group consisting of linear or branched $C_1$-$C_4$ alkyl,
or a stereoisomer thereof.

2. The compound according to claim 1 of formula (Ia)
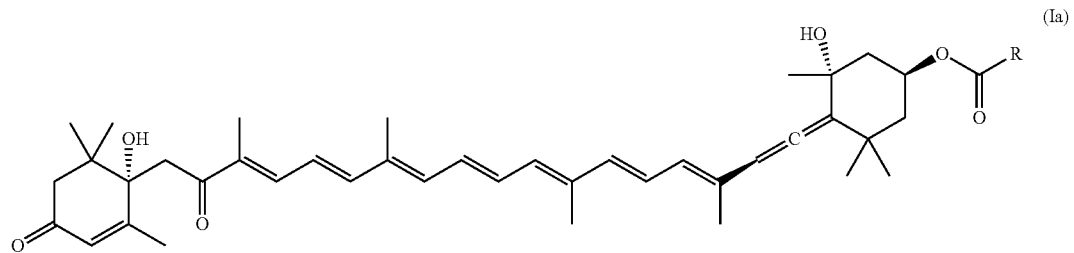
wherein R is as defined in claim 1.
3. The compound according to claim 1, wherein R is methyl.
4. A process for preparing a compound as defined in claim 1, which comprises:
a) reacting a compound of formula (II) or (IIa)
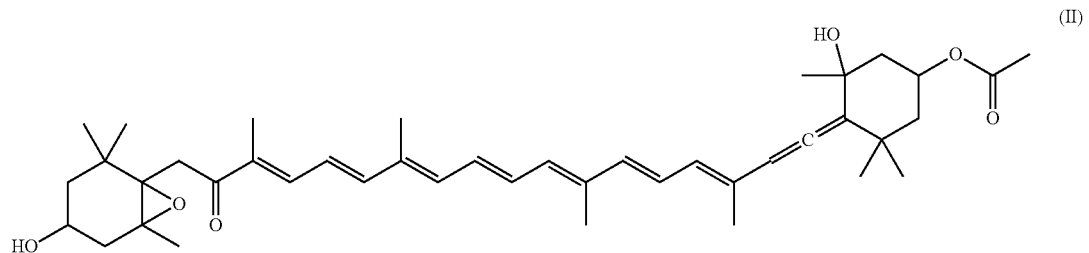
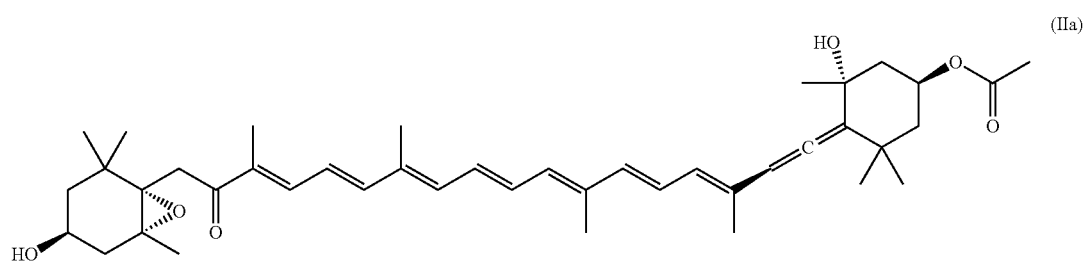
with an oxidant and optionally also in the presence of a co-oxidant to give a compound of formula (III) or (IIIa)
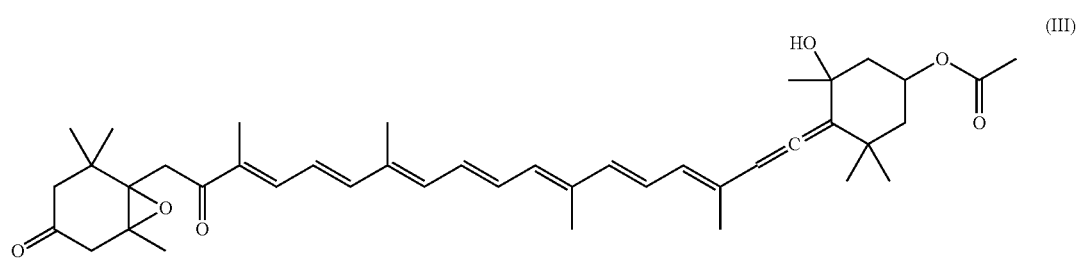

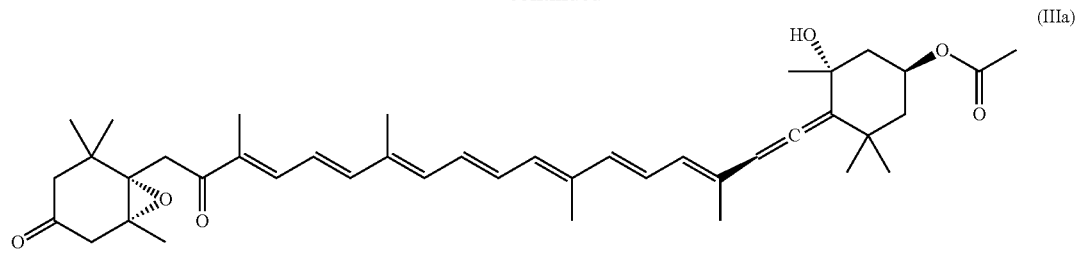

(IIIa)

b) treating the compound of formula (III) or (IIIa) with SiO$_2$ in the presence of a base to give a compound of formula (I) or (Ia) wherein R is methyl, and
c) wherein if the compound of formula (I) or (Ia) R is a linear or branched C$_2$-C$_4$ alkyl, the process further comprises:
  c1) converting the compound of formula (I) or (Ia) wherein R is methyl to a compound of formula (IV) or (IVa)

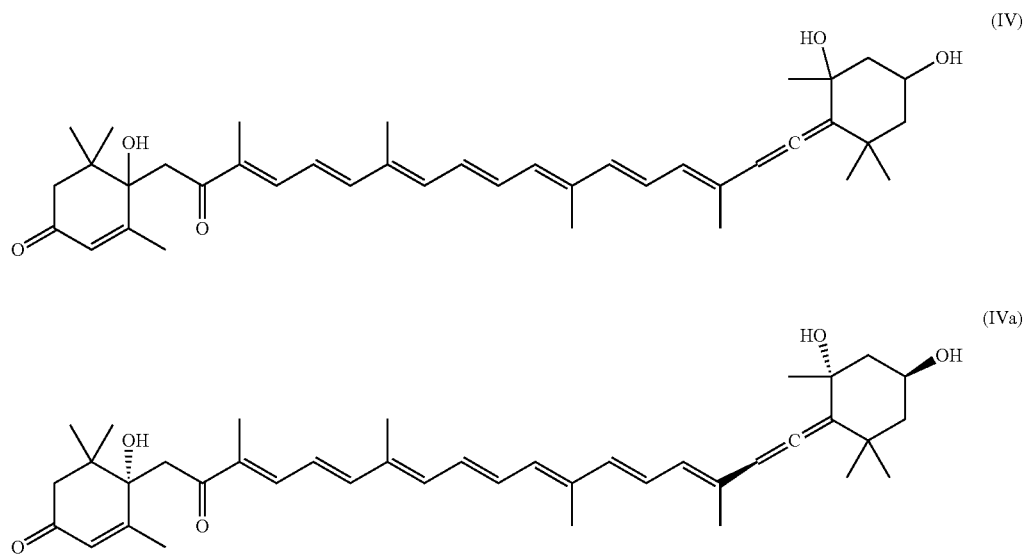

by treatment with an esterase and
c2) esterification of the compound of formula (IV) or (IVa) with a carboxylic acid of formula (V)

wherein R is a linear or branched C$_2$-C$_4$ alkyl, in the presence of a coupling agent selected from the group consisting of dicyclohexylcarbodiimide (DDC), diisopropylcarbodiimide (DIC) and ethyl-(N',N'-dimethylamino)propylcarbodiimide (EDC) or a salt thereof, and in the presence of 4-(dimethylamino)pyridine (DMAP), to give a compound of formula (I) or (Ia)

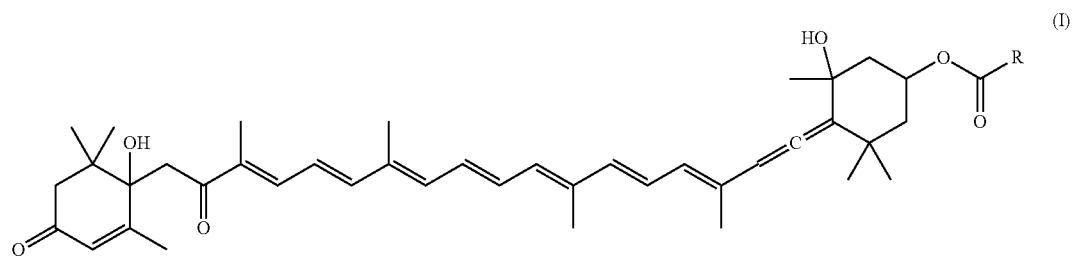

-continued

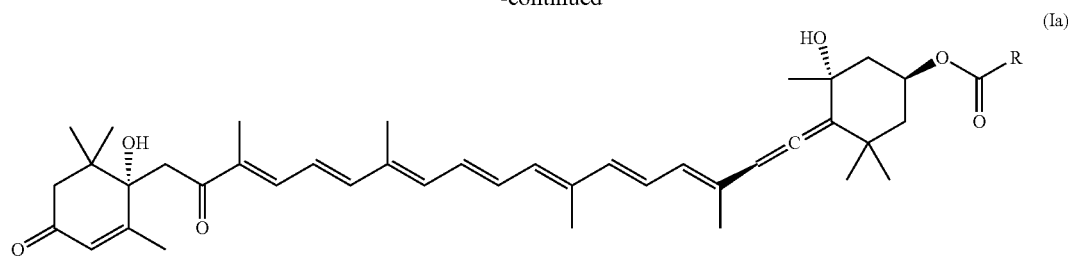

(Ia)

wherein R is selected from the group consisting of linear or branched $C_2$-$C_4$ alkyl.

5. The process of claim 4, wherein:
the oxidant of step a) is TPAP,
step a) is carried out in the presence of a co-oxidant,
the co-oxidant in step a) is NMO; and/or
the base in step b) is N-methylmorpholine.

6. The process of claim 4 wherein if step a) and/or b) is carried out in the presence of water, then a mixture of a compound as defined in claim 1 and a compound of formula (VI)

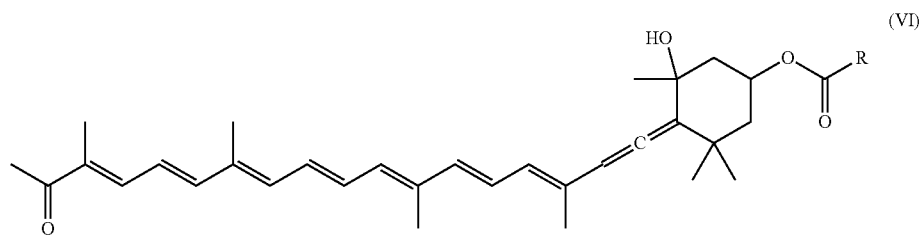

(VI)

wherein R is as defined in claim 1, is obtained.

7. The process for preparing amarouciaxanthin A comprising treating the compound according to claim 1 with an esterase.

8. A composition comprising a compound of formula (I)

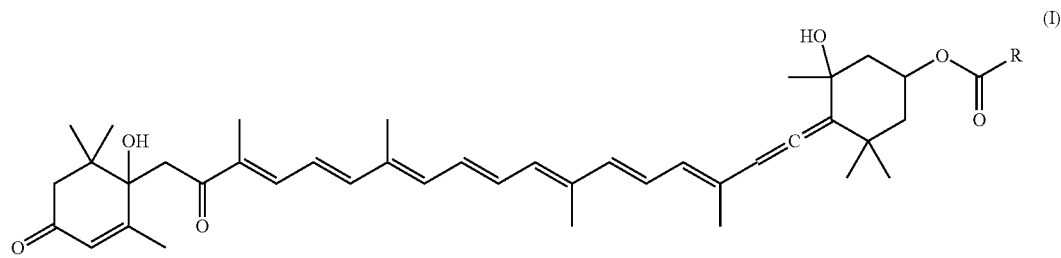

(I)

and a compound of formula (VI)

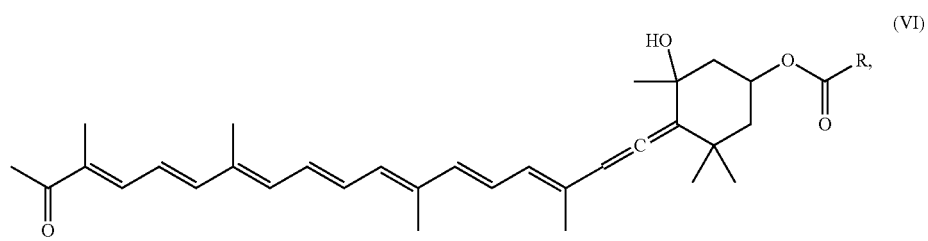

(VI)

and preferably of formula (VIa)

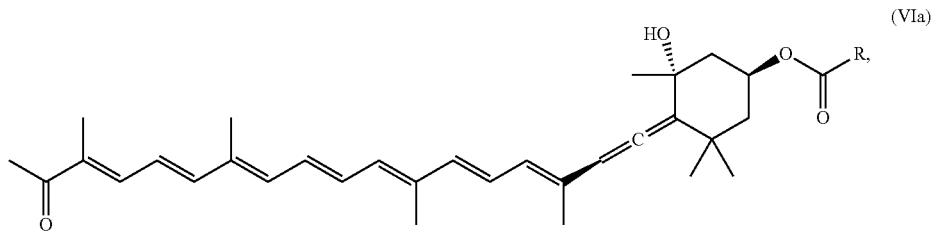

wherein R is selected from the group consisting of linear or branched $C_1$-$C_4$ alkyl, or a stereoisomer thereof.

9. A pharmaceutical composition comprising a compound according to claim 1.

10. A food, a cosmeceutical, a nutraceutical, or a cosmetic composition comprising a compound according to claim 1.

11. A cosmetic method for preventing or decreasing cutaneous senescence or for ameliorating the cosmetic adverse effects of aging comprising administering the compound according to claim 1, to a subject in need thereof.

12. A pharmaceutical composition comprising a composition according to claim 8.

13. A food, a cosmeceutical, a nutraceutical, or a cosmetic composition comprising a composition according to claim 8.

14. A cosmetic method for preventing or decreasing cutaneous senescence or for ameliorating the cosmetic adverse effects of aging comprising administering the composition according to claim 8, to a subject in need thereof.

* * * * *